United States Patent [19]
Wells et al.

[11] Patent Number: 5,330,971
[45] Date of Patent: Jul. 19, 1994

[54] GROWTH HORMONE FUSION PROTEINS, METHODS OF PRODUCTION, AND METHODS OF TREATMENT

[75] Inventors: Julian R. E. Wells, College Park; Robert M. King, Unley; Geoffrey L. Francis, Athelstone, all of Australia

[73] Assignee: GroPep Pty. Ltd., Thebarton, Australia

[21] Appl. No.: 646,616

[22] PCT Filed: May 22, 1990

[86] PCT No.: PCT/AU90/00210

§ 371 Date: Jan. 22, 1991

§ 102(e) Date: Jan. 22, 1991

[87] PCT Pub. No.: WO90/15142

PCT Pub. Date: Dec. 13, 1990

[30] Foreign Application Priority Data

Jun. 9, 1990 [AU] Australia ............... PJ 4672

[51] Int. Cl.$^5$ ........................... A01N 37/18
[52] U.S. Cl. ..................................... 514/2
[58] Field of Search .................. 536/23.4, 23.51; 435/69.1, 69.7, 320.1, 252.33; 530/350, 399; 514/2, 12

[56] References Cited

U.S. PATENT DOCUMENTS

| | | | |
|---|---|---|---|
| 5,019,500 | 5/1991 | Ueda et al. | 435/69.1 |
| 5,028,531 | 7/1991 | Ueda et al. | 435/69.4 |
| 5,077,276 | 12/1991 | Ballard et al. | 514/12 |

FOREIGN PATENT DOCUMENTS

| | | |
|---|---|---|
| 21796/88 | 3/1989 | Australia . |
| 266057 | 5/1988 | European Pat. Off. . |
| 307285 | 3/1989 | European Pat. Off. . |
| 1-144981 | 6/1989 | Japan . |
| 89/05822 | 6/1989 | World Int. Prop. O. . |

OTHER PUBLICATIONS

Henderson, E., *Henderson's Dictionary of Biological Terms*, 10th Edition, Longman Scientific and Technical, UK, 1989, p. 216.
Ballard, F. J. et al. in *Modern Concepts of Insulin-Like Growth Factors*, Elsevier Science Publishing, 1991, pp. 617–627.
Read, L. C. et al. in *Modern Concepts of Insulin-Like Growth Factors*, Elsevier Science Publishing, 1991, pp. 225–234.
Tomas, F. M. et al., *Biochem. J.*, 282:91–97, 1992.
Read, L. C. et al., *Proceedings of the Nutrition Society of New Zealand*, 17:136–143, 1992.
Read, L.C. et al., *J. of Endocrinology*, 133:421–31, 1992.
Ballard, F. J. et al., *Growth Regulation*, 3(1),:40–44, 1993.
Ballard, F. J. et al., *Aust. J. Agric. Res.*, 44:1–11, 1992.
Tomas, F. M. et al., *Biochem. J.*, 291:1–6, 1993.
Francis, G. L. et al., *J. of Mol. Endocrinology*, 8:213–223, 1992.
Sproat, B. S., *NAR*, 13(8):2959–2979, 1985.
Kadonaga, J. T. et al., *Cell*, 51:1079–1090, 1987.
D'Andrea, G. et al., *NAR*, 9(13):3119–3128, 1981.
Humbel, R., *Eur. J. Biochem.*, 190:445–462, 1990.
Brosius et al., *J. Biol. Chem.*, 260, 3539–3541 (1985).
Carter et al., *Proteins: Structure, Function, and Genetics*, 6, 240–248, (1989).

(List continued on next page.)

Primary Examiner—Robert J. Hill, Jr.
Assistant Examiner—Marianne Porta Allen
Attorney, Agent, or Firm—Merchant, Gould, Smith, Edell, Welter & Schmidt

[57] ABSTRACT

A plasmid encoding a fusion protein comprising a first polypeptide having growth hormone activity and a second polypeptide which may be one of insulin growth factor (IGF)-I or IGF-II and their analogues, chicken histone H2A.I or human transcription factor SPI-lac Z with an optional cleavage sequence between the first and second polypeptides. The fusion protein may be used: 1) to treat growth hormone deficiencies; 2) to suppress loss of body protein following trauma such as burns or infection; 3) for farm animals to increase growth rates and efficiency of food conversion; 4) and to support growth of cells in culture.

9 Claims, 4 Drawing Sheets

OTHER PUBLICATIONS

Amman et al., *Gene*, 40, 1983–190 (1985).
Messing, *Recomb. DNA Tech. Bull.*, 2 43–48 (1979).
Francis et al., *Biochem. J.*, 233, 207–213 (1986).
Rinderknecht et al., *FEBS Lett.*, 89, 283–286 (1978).
Ballard et al., *Aust. J. Agric. Res.*, 44, 1–11 (1992).
Cascieri, M. A. et al., *Endocrinology*, 122(4):1314–1320, 1988.
Misaka, F. et al., *Biotechnology Letters*, 11(12):839–44, 1989.
Moore, H. H. et al., *Nature*, 321:443–446, 1986.
Bayne, M. L. et al., *PNAS*, 84:2638–42, 1987.
Iwai, S. et al., *Chem. Pharm. Bull.*, 34(11):4724–4730, 1986.
Bagley, C. J. et al., *Biochem. J.*, 259:665–671, 1989.
Ballard, F. J. et al., *Biochem. Biophys. Res. Comm.*, 149(2):398–404, 1987.
Vize, P. D. et al., *FEBS Letters*, 213(1):155–58, 1987.
Vize, P. D. et al., *Gene*, 55:339–44, 1987.
Nishikawa, S. et al., *Protein Engineering*, 1(6):487–92, 1987.

GROWTH HORMONE FUSION PROTEINS, METHODS OF PRODUCTION, AND METHODS OF TREATMENT

This invention relates to growth factors, their production as fusion proteins and use as well as to the production of other proteins as fusion proteins. As used herein, the term methionine porcine growth hormone (metpGH) means porcine growth hormone in which methionine has been substituted for the amino acid normally at the N-terminus.

Insulin-like growth factor-I (IGF-I) is a small protein that has been shown to stimulate the growth of a wide range of cells in culture. Animal growth is also stimulated in pituitary-deficient, normal and catabolic states.

Human, bovine and porcine IGF-I all share the identical sequence, shown here using the single letter amino acid code and numbering from the amino terminus:

```
1         2         3         4         5         6         7
0         0         0         0         0         0         0
GPETLCGAELVDALQFVCGDRGFYFNKPTGYGSSSRRAPQTGIVDECCFRSCDLRRLEMYCAPLKPAKSA
```

The animal and cell growth results have lead to the interpretation that IGF-I may usefully be applied:
(1) in humans to treat growth hormone deficiencies;
(2) in humans to suppress the 10ss of body protein in severe catabolic states such as following burns, infection or other trauma;
(3) in farm animals to increase growth rates, redistribute nutrients and enhance food conversion efficiency; and
(4) to support the growth of cells in culture.

There is accordingly a commercial demand for mammalian IGF-I for use in animal growth trials, clinical investigations and for cell culture. However, yields from natural sources and/or from recombinant DNA synthesis methods remain low.

Accordingly it is an object of the present invention to overcome or at least alleviate one or more of the difficulties related to the prior art.

Accordingly in a first aspect of the present invention there is provided a plasmid including
a suitable expression vector;
a first DNA sequence coding for a first polypeptide having growth hormone activity, or fragment thereof; and
a second DNA sequence joined to the 3' end of the first DNA sequence and coding for a second polypeptide.

It will be understood that the constructs so formed may express fusion proteins in inclusion bodies in high yields and exhibiting biological activity comparable to those in the prior art developed for growth hormone alone. Disruption of the organisms, isolation of the fusion protein from the inclusion bodies, oxidation to achieve correct disulphide bonds and purification may yield an extended polypeptide, for example a biologically active insulin-like growth factor. If sequences coding for a clearable sequence are introduced at the 3' end of the first DNA sequence, the addition of a cleavage step may yield a polypeptide that is not extended.

The suitable cloning vector may be selected from plasmid cloning vectors. The plasmid cloning vectors may be utilized in the process for production of insulin-like growth factor fusion proteins in high yield as discussed below. The plasmid cloning vector may be plasmid pGHXSC.4 that has a modified RBS/spacer region and strategic 5'-codon alterations downstream from the powerful trc promoter (J. Brosius et al. J. Biol. Chem. 260, 3539, 1985; P. D. Vize & J. R. E. Wells, FEBS Lett. 213, 155, 1987).

The first DNA sequence coding for a peptide having growth hormone activity or fragment thereof may code for a peptide having porcine growth hormone (pGH) activity. A methionine porcine growth hormone sequence (metpGH or MpGH) is preferred. The first DNA sequence may code for all 191 N-terminal amino acids of metpGH or any fragment thereof. The first DNA sequence may code for approximately the first 100 N-terminal amino acids of metpGH, more preferably approximately the first 46 N-terminal amino acids, most preferably the first 11 N-terminal amino acids of metpGH.

In a preferred aspect of the present invention, the first DNA sequence may include a clearable sequence at the 3' end thereof.

Specifically, in a preferred aspect of the present invention the first DNA sequence codes for an amino acid sequence selected from
MFPAMPLSSLFANAVLRAQHLHQLAAD-TYKEFERAYIPEGQRYSIQ-,
MFPAMPLSSLFANAVLRAQHLHQLAAD-TYKEFERAYIPEGQRYSIQVN- or
MFPAMPLSSLFANAVLRAQHLHQLAAD-TYKEFERAYIPEGQRYSIQVNFAHY-.

These sequences represent, in order, the initiating methionine, the first 46 amino acids of pGH, valine, asparagine, phenylalanine, alanine, histidine and tyrosine.

In an alternate preferred aspect of the present invention the first DNA sequence codes for an amino acid sequence selected from:
MFPAMPLSSLF-,
MFPAMPLSSLFVN-,
MFPAMPLSSLFVNFAHY- or
MFPAMPLSSLFVNGFAHY-.

These sequences represent, in order, the initiating methionine, the first 10 amino acids of pGH, valine, asparagine, glycine, phenylalanine, alanine, histidine and tyrosine.

It will be recognized by those familiar with the art that in these examples the C-terminal asparagine provides a hydroxylamine clearable site when linked to a peptide having an N-terminal glycine. Such a peptide is IGF-I. It will be further recognized that the phenylalanine-alanine-histidine-tyrosine (FAHY) peptide provides a cleavable site when linked to peptides with most N-terminal amino acids (P. Carter et al. Proteins-Structure Function and Genetics 6, 240, 1989). This site may be cleaved C-terminally by the mutant subtilisin enzyme, subtilisin-BPN'.

The second DNA sequence coding for a polypeptide may code for a polypeptide having biological activity. The second DNA sequence may code for a peptide having insulin-like growth factor activity. The insulin-like growth factor may be an insulin-like growth factor-I (IGF-I). Peptides other than IGF-I may be used and the references below to IGF-I should be understood as illustrative only. For example, the second DNA sequence coding for a polypeptide may be selected from
IGF-I including human IGF-I and IGF-I from species other than human,
IGF-I analogues including analogues formed with amino acid substitutions or deletions such as those specified in co-owned international applications PCT/AU86/00246 and PCT/AU88/00485,
insulin-like growth factor-II (IGF-II); or IGF-II analogues thereof,
chicken histone H2A.1, or
human transcription factor SPi-lac Z fusion protein may be used.

Accordingly, in a preferred aspect of the present invention there is provided plasmids
pMpGH(46)VN/IGF-I
pMpGH(46)VN/G3IGF-I
pMpGH(46)VN/R3IGF-I
pMpGH(46)VNFAHY/chicken histone H2A.1
pMpGH(46)/human transcription factor Spl-lac Z fusion protein
pMpGH(42)FAHY/des(1-3)IGF-I
pMpGH(11)VN/IGF-I
pMpGH(11)VN/G3IGF-I
pMpGH(11)VN/R3IGF-I
pMpGH(11)VNGFAHY/des(1-3)IGF-I
pMpGH(11)VNGFAHY/IGF-I
pMpGH (11)VNFAHY/chicken histone H2A.1
pMpGH (11)/human transcription factor Spl-lac Z fusion protein.

Accordingly in a further aspect of the present invention there is provided a process for the production of fusion proteins which process includes
providing a plasmid including
a suitable expression vector;
a first DNA sequence coding for a first polypeptide having growth hormone activity, or fragment thereof;
a second DNA sequence joined to the 3' end of the first DNA sequence and coding for a second polypeptide; and
a unicellular organism;
introducing said plasmid into said unicellular organism;
culturing the resulting organism;
expressing the polypeptide encoded by said DNA sequences; and
isolating said polypeptide from the culture.

In the process according to this aspect of the present invention, the unicellular organism may be a prokaryotic organism. The prokaryotic organism may be a bacterial strain, such as a strain of E. coli. The E. coli strain, E. coli JM101 has been found to be particularly suitable.

The plasmids for use in this aspect of present invention may be any of the plasmids described above.

Samples of E. coli containing the plasmids specifically described herein are maintained in the cell culture collection of the University of Adelaide, North Terrace, Adelaide, South Australia, Australia.

The production steps of the process according to the present invention may be carried out using well known methodology, for example as illustrated in the examples hereinafter.

The plasmid may be introduced into the unicellular organism by any method known per se. For example, transformation, transduction or transfection techniques may be used.

Where it is desired to isolate the polypeptide product, conventional procedures may be used thus, after cell disruption, e.g. by cell lysis. The isolation step for the fusion protein may be conducted utilising, for example, chromatography involving ion exchange, affinity, reversed phase or sizing techniques and/or by sedimentation, e.g. centrifugation, or by other known techniques for the purification of polypeptides.

Where the fusion protein is expressed as an insoluble aggregate and/or is denatured, solubilization and/or renaturation may be effected utilizing conventional techniques.

In a preferred aspect of the process of the present invention, the process may include the preliminary step of introducing coding for a clearable bond between the first and second DNA sequences in the vector.

Accordingly the process of the present invention may further include the preliminary steps of
providing
a plasmid including a suitable expression vector;
a first DNA sequence coding for a first polypeptide having growth hormone activity, or fragment thereof contained therein; and
a second DNA sequence joined at the 3' end of the first DNA sequence and coding for a second polypeptide;
digesting the plasmid DNA to isolate a fragment of DNA including the expression vector and the first DNA sequences;
subjecting the first DNA sequence to mutagenesis to introduce a cleavable sequence at the 3' end thereof; and
ligating the fragment containing the expression vector and the first DNA sequence to the second DNA sequence.

The digestion may optionally include a subsequent purification step to provide a purified DNA fragment.

The suitable plasmid expression vector may be of any suitable type. The plasmid pGHXSC.4 may be used. The plasmid pGHXSC.4 includes the pGH coding region.

The second DNA sequence may be provided from natural or synthetic sources. Thus in accordance with a further preferred aspect of the present invention the process may further include
the preliminary step of chemically synthesising the second DNA sequence.

The chemical synthesis may be undertaken in any conventional manner.

The digestion and ligation steps may be undertaken in any conventional manner.

The mutagenesis step may be an in vitro mutagenesis. The in vitro mutagenesis reaction may utilize a suitable oligomer nucleotide to introduce a clearable bond between the first and second DNA sequences. A hydroxylamine clearable bond may be introduced. Alternatively or additionally a subtilisin clearable cond may be introduced.

If desired, mutagenesis steps may be included to reduce the size of the growth hormone coding sequence and/or to introduce a recognition site to facilitate additional mutagenesis steps.

Thus in accordance with a further preferred aspect of the present invention the process of the present invention may further include the preliminary steps of
providing
a plasmid including a suitable expression vector;

a first DNA sequence coding for a first polypeptide having growth hormone activity, or fragment thereof contained therein; and a second DNA sequence joined at the 3' end of the first DNA sequence and coding for a second polypeptide;

digesting the plasmid DNA to isolate a fragment of DNA including the expression vector and the first DNA sequences;

subjecting the first DNA sequence to mutagenesis to reduce the size of the growth hormone coding sequence and/or to introduce a recognition site; and ligating the fragment containing the expression vector and the first DNA sequence to the second DNA sequence.

Preferably the mutagenesis step includes subjecting the first DNA sequence to an in vitro mutagenesis utilizing an oligomer nucleotide selected from a second amino acid sequence having biological activity, joined to the C-terminal of the first amino acid sequence.

In a preferred form, the first amino acid sequence is a methionine porcine growth hormone sequence, or fragment thereof.

In a further preferred form, the second amino acid sequence is selected from
insulin-like growth factor-I (IGF-I),
IGF-I analogues,
insulin-like growth factor-II (IGF-II) or IGF-II analogues thereof,
chicken histone H2A.1, or
human transcription factor SP1-lac Z fusion protein.

In a particular preferred form there is provided a fusion protein exhibiting insulin-like growth factor activity including
a first amino acid sequence having growth hormone "OLIGO 42 mer":
5'-CAGGGTTTCCGGGCCGTTGAAGGCACAGCTGCTCTCCACGAA-3'
"OLIGO-46":
5'-GCACAGGGTTTCCGGGCCGTTAACCTGGATGGAGTACCTCTGTCC-3'
"OLIGO-11":
5'-GCACAGGGTTTCCGGGCCGTTAACAAATAGGCTGGACAAGGGCAT-3'
"OLIGO-756":
5'-ACCGCACAGGGTACGCGGGCCGTTAAC-3'
"OLIGO-713":
5'-AGCACCGCACAGGGTATAATGGGCGAACCTCTGTCCCTCCGGGAT-3'
"OLIGO-818":
5'-ATAATGGGCGAAACCGTTAACCCTCTGTCCCTC-3', and
"OLIGO":
5'-TTCAGTCGCTGCGATGTTAACTTCGCCCATTATTCGGGGCGCGGAAAG-3'.

The fusion proteins formed according to this aspect of the present invention, may be isolated as inclusion bodies within the engineered unicellular organisms. The fusion proteins may be subjected to further processing steps as required.

If desired, in accordance with a further embodiment of the present invention the process may further include the step of cleaving a cleavable bond between the first and second DNA sequences.

Such cleavage may be conducted in any conventional manner. The fusion proteins so generated may be extracted from the inclusion bodies, cleaved at either the hydroxylamine-clearable, asparagine/glycine bond or the subtilisin-cleavable bond following the sequence FAHY and the resultant IGF-I or substitute peptide oxidised, and purified by techniques familiar to those knowledgable of the prior art.

It has been found that the process as described above may produce biologically active insulin-like growth factors in high yield.

It has surprisingly been found, however, that cleavage of the sequences to remove the growth hormone residue may not be required to achieve adequate biological activity, where the growth hormone fragment is small. For example, where the growth hormone sequence includes approximately 10 amino acids, then cleavage of the growth hormone residue may not be required.

The fusion proteins so formed may be utilized in any of the various applications known per se for the polypeptides so formed, for example insulin-like growth factor-I. Thus in a further aspect of the present invention there is provided a fusion protein including a first amino acid sequence having growth hormone activity, or a fragment thereof; and activity, or a fragment thereof; and a second amino acid sequence having insulin-like growth factor activity or an analogue thereof, joined to the C-terminal of the first amino acid sequence.

The first and second amino acid sequences may be linked together by a cleavable bond, preferably a hydroxylamine-cleavable bond or a subtilisin-cleavable bond.

The second amino acid sequence may exhibit insulin-like growth factor-I or -II activity. The second amino acid sequence may exhibit activity of analogues of insulin-like growth factor-I with deletions or substitutions in the sequence. Such deletions or substitutions may include but are not limited to substitutions or deletions near the N-terminal of insulin-like growth factor-I (IGF-I). For example certain analogues have been shown to exhibit a substantial increase in biological potency compared with insulin-like growth factor-I. (See for example international applications PCT/AU86/00246 and PCT/AU88/00485 to the applicants). The insulin-like growth factor-I may be a mammalian insulin-like growth factor-I. A human, bovine or porcine insulin-like growth factor-I may be used.

The first amino acid sequence may exhibit porcine growth hormone activity. The porcine growth hormone may be a methionine porcine growth hormone (metpGH or MpGH). Amino acid sequence may include all 191 N-terminal amino acids of metpGH joined at its C-terminus to the N-terminus of the growth factor sequence or may include fragments thereof.

The first amino acid sequence may include approximately the first 100 N-terminal amino acids of metpGH, more preferably approximately the first 46 N-terminal amino acids of metpGH or approximately the first 42 N-terminal amino acids of metpGH, most preferably approximately the first 11 N-terminal amino acids of metpGH. Specifically, in a preferred aspect of the present invention the first amino acid sequence is selected from the following MFPAMPLSSLF -,
MFPAMPLSSLFVN -,
MFPAMPLSSLFVNFAHY- or
MFPAMPLSSLFVNGFAHY-.

The fusion protein may be provided in a biologically pure form.

The fusion proteins according to the preferred aspects of the present invention may form suitable replacements for IGF-I :

(1) in humans to treat growth hormone deficiencies;
(2) in humans to suppress the loss of body protein in severe catabolic states such as following burns, infection or other trauma;
(3) in farm animals to increase growth rates, redistribute nutrients and enhance food conversion efficiency, and
(4) to support the growth of cells in culture.

More specifically, the fusion protein may be administered to promote growth and improve food conversion efficiency in economic, warm-blooded animals, including cattle, sheep, pigs and chickens. The modified fusion protein may be administered alone or with various diluents, carriers or excipients that have been chosen with respect to the intended method of administration.

Accordingly, in a further aspect, the present invention provides a pharmaceutical or veterinary composition for the treatment of protein accumulation deficiencies or protein loss in mammals including an effective amount of (a) a fusion protein exhibiting insulin-like growth factor activity including
  a first amino acid sequence having growth hormone activity or a fragment thereof; and
  a second amino acid sequence having insulin-like growth factor activity or an analogue thereof, joined to the C-terminal of the first amino acid sequence; and
(b) a pharmaceutically or veterinarily acceptable diluent, carrier or excipient therefor.

If required, the second amino acid sequence may be cleaved from the first amino sequence.

In a further preferred form the present invention provides a composition wherein the fusion protein is present in amounts sufficient to provide a dose rate of approximately 0.01 to 10, preferably 0.1 to 1 milligrams/kg body weight/day. The fusion protein may be present, in a unit dosage form, in amounts of from approximately 0.02 to 2000 milligrams.

Slow-release, pellet implants are the preferred method of administration to animals of economic importance as applied in conventional practice.

Accordingly in a still further aspect of the present invention, there is provided a method for the treatment of protein accumulation deficiencies in mammals which method includes administering to a patient to be treated an effective amount of a fusion protein exhibiting insulin-like growth factor activity including
  a first amino acid sequence having growth hormone activity or a fragment thereof; and
  a second amino acid sequence having insulin-like growth factor activity or an analogue thereof, joined to the C-terminal of the first amino acid sequence.

The treatment may also be applied to protein loss in mammals.

The fusion proteins of the present invention may be administered to human subjects as a treatment for chronic growth disorders including growth hormone deficiency and somatomedin deficiencies. The modified IGF-I may be administered parenterally for this purpose, or using procedures outlined above for use with economic animals.

The fusion proteins may be administered to human subjects as a treatment for disorders associated with insufficient growth or tissue wasting including, but not limited to, cancer, cystic fibrosis, Duchenne muscular dystophy, Becker dystrophy, autosomal recessive dystrophy, polymyositis as well as other myopathies. The modified IGF-I peptides may be administered using procedures given above for growth disorders.

The fusion proteins, may be administered to human subjects as a treatment for acute conditions associated with poor nitrogen status including, but not limited to, burns, skeletal trauma and infection. Although the preferred method of administeration may be via addition to parenteral fluids in these critical care situations, other procedures such as those listed above for growth disorders may be appropriate.

The fusion proteins of the present invention may be administered to premature or other human infants to promote growth, improve nitrogen status and to treat catabolic disorders. The proteins may be administered as outlined above for acute human conditions or by enteral routes.

The dose rates and times for the administration of the fusion proteins to human subjects may be set at approximately 0.01 to 10 milligrams/kilogram/day. Dose rates of approximately 0.1 to 1 milligrams/kilogram/day are preferred.

The present invention will now be more fully described with respect to the following examples. It should be understood, however, that the following description is illustrative only and should not be taken in any way as a restriction on the generality of the description foregoing.

In the Figures:

FIG. 1 shows SDSPAGE of inclusion bodies containing (A) MpGH(46)VN/IGF-I (Example 4), (B) MpGH(ll)VN/R³IGF-I (Example 6), (C) MpGH(ll)VNFAHY/des(1-3)IGF-I (Example 8) and (D) MpGH(42)FAHY/des(1-3)IGF-I (Example 7). Arrows show induced bands.

FIG. 2 A-B shows expression of (A) MpGH(46)VNFAHY/H2A.1 (Example 9) and (B) MpGH(46)/lac Z Spl (Example 10) in lysates of (U) uninduced and (I) IPTG-induced JM101 cultures. Arrows show induced bands.

EXAMPLE 1

Figure 1:
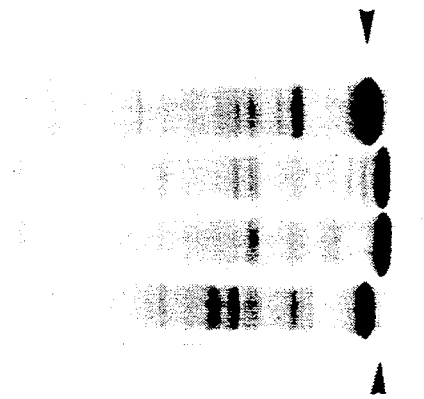

Cloning IGF-I sequence 3' to DGH sequence in pGHXSC.4

High yields of metpGH are expressed as inclusion bodies in *E. coli* JM101 cells containing the plasmid pGHXSC.4 that has a modified RBS/spacer region and strategic 5'-codon alterations (P. D. Vize & J. R. E. Wells, FEBS Lett. 213, 155, 1987).

pGHXSC.4 DNA was digested with PvuII to cut the metpGH DNA sequence at position 563 and with HindIII to cut in the polylinker sequence of pKT52, a bacterial expression vector derived from pKK233.2 (E. Amman & J. Brosius, Gene 40, 183, 1985), in which the pGH gene is cloned. The 3.4 kb fragment containing vector and most of the pGH gene was purified (a).

A chemically-synthesised metIGF-I structural gene optimised for bacterial codon usage (B. Sproat & M. Gait, Nucleic Acids Research 13, 2959, 1985) in M13mp8 was modified by in vitro mutagenesis to introduce an NcoI site (C↓CATGG) adjacent to the start codon:

TCC ATG GGC CCG —
Met. Gly. Pro

This modified metIGF-I in M13 was digested with NcoI and the sticky end was end-filled with Klenow before digestion of the DNA with HindIII. The blunt-HindIII fragment was purified and ligated to the vector (a) to create the first 188 amino acid coding region of metpGH followed by that for metIGF-I. This construct is termed pMpGH(188)MIGF-I and has the following interface sequence:

| 184 | 185 | 186 | 187 | 188 | 1 | 2 | 3 | 4 |
|---|---|---|---|---|---|---|---|---|
| Phe. | Val. | Glu. | Ser. | Ser. | Met. | Gly. | Pro. | Glu |
| — TTC | GTG | GAG | AGC | AGC | ATG | GGC | CCG | GAA — |
| metpGH | | | | | metIGF-I | | | |

EXAMPLE 2

Mutagenesis: replacement of missing pGH amino acids, removal of met and introduction of asn to create a hydroxylamine-cleavable metDGH.asn IGF-I construct (mMpGH(191)N/IGF-I)

In order to perform in vitro site-directed mutagenesis, relevant sequences had to be first cloned from the bacterial expression vector into a single stranded vector, such as M13mp8.

To this end, the EcoRI-HindIII fragment (containing the trc promoter of the expression vector, and the structural gene for the pGH-IGF fusion protein) of pMpGH(188)MIGF-I was cloned into EcoRI/HindIII cut M13mp8.

A recombinant phage from this ligation was used as template for the mutagenesis reaction. An oligonucleotide, 42 bases long

5'-CAGGGTTTCCGGGCCGTTGAAGG-CACAGCTGCTCTCCACGAA-3' was used in standard procedures to produce the desired sequence at the junction of pGH and IGF coding sequences:

| 187 | 188 | 189 | 190 | 191 | 1 | 2 | 3 | 4 |
|---|---|---|---|---|---|---|---|---|
| Ser. | Ser. | Cys. | Ala. | Phe. | Asn. | Gly. | Pro. | Thr. |
| — AGC | AGC | TGT | GCC | TTC | AAC | GCC | CCG | GAA ACC — |
| metpGH | | | | | IGF-I | | | |

This construct is called mMpGH(191)N/IGF-I. It codes for the entire sequence of metpGH, N-terminal to the IGF-I sequence with a potential hydroxylamine-clearable linkage at the junction.

EXAMPLE 3

Restriction enzyme deletion of C-terminal pGH-coding sequence from mMpGH(191)N/IGF-I In order to remove much of the terminal portion of pGH from the pGH-IGF fusion protein encoded by mMpGH(191)N/IGF-I, restriction enzymes AvaI and PvuII were used to remove 300 bp of pGH DNA sequence.

Because M13mp8 contains 2 AvaI sites, the EcoRI-HindIII fragment from mMpGH(191)N/IGF-I was first cloned back into EcoRI-HindIII cut pKT52. DNA from such a recombinant was digested with AvaI, the 5' overhanging end filled with Klenow enzyme, then digested with PvuII. The 3.3kb fragment containing vector, N-terminal pGH sequences and IGF sequences (blunt-ended) was purified and religated to give pMpGH(91)N/IGF-I. (This encodes the first 88 amino acids of metpGH, followed by the last 3 and then asn-IGF-I).

| 87 | 88 | 189 | 190 | 191 | 1 | 2 | 3 | 4 |
|---|---|---|---|---|---|---|---|---|
| Leu. | Gly. | Cys. | Ala. | Phe. | Asn. | Gly. | Pro. | Thr |
| — CTC | GGC | TGT | GCC | TTC | AAC | GGC | CCG | GAA ACC — |
| metpGH | | | | | IGF-I | | | |

EXAMPLE 4

Mutagenesis to create pMpGH(46)VN/IGF-I

The EcoRI-HindIII fragment from pMpGH(91)N/IGF-I was cloned into EcoRI-HindIII cut M13mp8.

The 45-mer "OLIGO-46":

5' - GCACAGGGTTTCCGGGCCGTTAACCT-GGATGGAGTACCTCTGTCC- 3' was synthesised to delete further the C-terminal portion of pGH sequences in pMpGH(91)N/IGF-I, introduce the recognition site for HpaI (GTT AAC) and maintain the −1 position of Asn in IGF-I. In this way mMpGH(46)VN/IGF-I was created:

| 44 | 45 | 46 | 1 | 2 | 3 | 4 |
|---|---|---|---|---|---|---|
| Ser. | Ile. | Gln. | Val. | Asn. | Gly. | Pro. | Glu. | Thr |
| — TCC | ATC | CAG | GTT | AAC | GGC | CCG | GAA | ACC — |
| | | | HPaI | | | |
| metpGH(1-46) | | | IGF-I | | | |

The EcoRI-HindIII insert from the replicarive form of DNA grown from mMpGH(46)VN/IGF-I was cloned into EcoRI-HindIII cut pKT52 to give pMpGH(46)VN/IGF-I.

EXAMPLE 5

Mutagenesis to create pMpGH(11)VN/IGF-I

This was carried out as described in example 4 except that the 45-mer "OLIGO-11":

5'-GCACAGGGTTTCCGGGCCGT-
TAACAAATAGGCTGGACAAGGGCAT-3'
was used to create mMpGH(11)VN/IGF-I:

| 1 | 2 | 3 | 4 | 5 | 6 | 7 | 8 | 9 | 10 | 11 | | 1 | 2 | 3 | 4 | |
|---|---|---|---|---|---|---|---|---|----|----|---|---|---|---|---|---|
| Met. | Phe. | Pro. | Ala. | Met. | Pro. | Leu. | Ser. | Ser. | Leu. | Phe. | Val. | Asn. | Gly. | Pro. | Glu. | Thr |
| ATG | TTC | CCA | GCC | ATG | CCC | TTG | TCC | AGC | CTA | TTT | GTT | ACC | GGC | CCG | GAA | ACC — |

| metpGH(I-II) | HpaI | IGF-I |
|---|---|---|

Similarly to example 4 the EcoRI-HindIII insert from the replicative form of DNA grown from mMpGH(11)VN/IGF-I was cloned into EcoRI-HindIII cut pKT52 to give pMpGH(11)VN/IGF-I.

EXAMPLE 6

Mutagenesis to create pMpGH(11)VN/R³IGF-I

Using single stranded DNA of mMpGH(46)VN/IGF-I (Example 4) as template and the synthetic 27-mer "OLIGO-756":
5'-ACCGCACAGGGTACGCGGGCCGTTAAC-3'
in an in vitro mutagenesis reaction, mMpGH(46)VN/R³-IGF-I was created:

| 44 | 45 | 46 | | 1 | 2 | 3 | 4 | 5 |
|---|---|---|---|---|---|---|---|---|
| Ser. | Ile. | Gln. | Val. | Asn. | Gly. | Pro. | Arg. | Thr. | Leu |
| — TCC | ATC | CAG | GTT | AAC | GGC | CCG | CGT | ACC | CTG — |

| metpGH(1-46) | HpaI | R³IGF-I |
|---|---|---|

The HpaI-HindIII fragment from the replicative form DNA of this vector was ligated to pMpGH(11)VN/IGF-I (Example 5) cut with HpaI and HindIII to create pMpGH(11)VN/R³IGF-I:

| 1 | 2 | 3 | 4 | 5 | 6 | 7 | 8 | 9 | 10 | 11 | | 1 | 2 | 3 | 4 | 5 | 6 |
|---|---|---|---|---|---|---|---|---|----|----|---|---|---|---|---|---|---|
| Met. | Phe. | Pro. | Ala. | Met. | Pro. | Leu. | Ser. | Ser. | Leu. | Phe. | Val. | Asn. | Gly. | Pro. | Arg. | Thr. | Leu |
| ATG | TTC | CCA | GCC | ATG | CCC | TTG | TCC | AGC | CTA | TTT | GTT | AAC | GGC | CCG | CGT | ACC | CTG — |

| metpGH(1-11) | HpaI | R³IGF-I |
|---|---|---|

EXAMPLE 7

Mutagenesis to create pMpGH(42)FAHY/des(1-3)IGF-I

Single stranded DNA from mMpGH(46)VN/IGF-I (see Example 4), and the synthetic 45-mer "OLIGO-713":
5'-AGCACCGCACAGGGTATAATGGG-
CGAACCTCTGTCCCTCCGGGAT-3'
were used in an in vitro mutagenesis reaction to create mMpGH(42)FAHY/des(1-3)IGF-I:

| 40 | 41 | 42 | | | 4 | 5 | 6 |
|---|---|---|---|---|---|---|---|
| Gly. | Gln. | Arg. | Phe. | Ala. | His. | Tyr. | Thr. | Leu. | Cys |
| —CGA | CAG | AGG | TTC | GCC | CAT | TAT | ACC | CTG | TGC— |

| metpGH(1-42) | Subtilisin-BPN' recognition and cleavage site | des(1-3)IGF-I |
|---|---|---|

The EcoRI-HindIII fragment from the replicative form DNA of this vector was ligated to EcoRI-HindIII cut pKT52 to create pMpGH(42)FAHY/des(1-3)IGF-I.

EXAMPLE 8

Mutagenesis to create pMDGH(11)VNGFAHY/des(1-3)IGF-I

Single stranded DNA of mMpGH(42)FAHY/des(1-3)IGF-I (see Example 7) and the synthetic 33-mer "OLIGO 818":
5'-ATAATGGGCGAAACCGT-
TAACCCTCTGTCCCTC-3'
were used in an in vitro mutagenesis reaction to create mMpGH(42)VNGFAHY/des(1-3)IGF-I:

| 40 | 41 | 42 | | | | | 4 | 5 | 6 |
|---|---|---|---|---|---|---|---|---|---|
| Gly. | Gln. | Arg. | Val. | Asn. | Gly. | Phe. | Ala. | His. | Tyr. | Thr. | Leu. | Cys |
| — GGA | CAG | AGG | GTT | AAC | GGT | TTC | GCC | CAT | TAT | ACC | CTG | TGC — |

| metpGH(1-42) | HpaI | Subtitisin-BPN' recognition and cleavage site | des(1-3)IGF-I |
|---|---|---|---|

The HpaI-HindIII fragment from the replicative form DNA of this vector was ligated to pMpGH(11)VN/IGF-I (Example 5) cut with HpaI and HindIII to create pMpGH(11)VNGFAHY/des(1-3)-IGF-I.

EXAMPLE 9

Production of the plasmid pMpGH(46)VNFAHY/chicken histone H2A.1

A HindIII fragment (approx. 700 bp) from pCH.H2AH (D'Andrea et al. Nucl. Acids Res. 9, 3119, 1981) was subcloned into the phagemid vector Bluescript KS+ (Stratagene Inc.) cut with HindIII. Single stranded DNA prepared from this clone was used as template for mutagenesis. The "OLIGO":
5'-TTCAGTCGCTGCGATGTTAACTTCGC-
CCATTATTCGGGGCGCGGAAAG-3'
was used to introduce by mutagenesis the indicated sequence after the start codon of the template as follows:

| | Met. | Ser. | Gly. | Arg. | Gly. | Lys |
|---|---|---|---|---|---|---|
| 5'-TGTTCAGTCGCTGCGATG | TCG | GGG | CGC | GGA | AAG-3' |

| Val. | Asn. | Phe. | Ala. | His. | Tyr |
|---|---|---|---|---|---|
| (G)TT | AAC | TTC | GCC | CAT | TAT |

HpaI

The mutant clone was selected, double stranded DNA prepared, cut with HpaI and HindIII, after which the fragment was cloned into pMpGH(46)VN/IGF-I (Example 4) from which the HpaI-HindIII fragment (IGF-I sequence) had been removed to give pMpGH(46)VNFAHY/chicken histone H2A.1.

EXAMPLE 10

Production of the plasmid pMpGH(46]/human transcription facter Spl-lac Z fusion protein The plasmid pSpl-516C (coding for the C-terminal 516 amino acid portion of Spl) was made by cloning a HincII-HindIII fragment from the cDNA clone pSpl (J. Kadonaga et al. Cell, 51. 1079, 1987) into pUCl18 cut with SmaI and HindIII. The DNA of pSpl-516C with the following sequence:

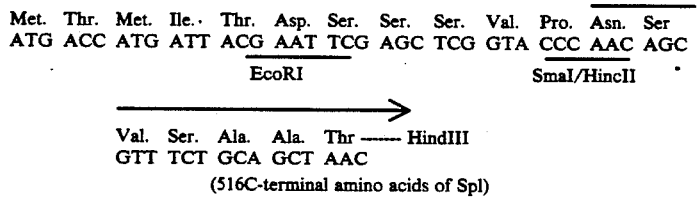

was digested with EcoRI, end-filled with Klenow and then digested with HindIII to give a fragment (blunt-HindIII) that coded for sequences 6-11 of met-lac Z and all 516 C-terminal amino acids of Spl. This fragment was cloned into pMpGH(46)VN/IGF-I (Example 4) from which the HpaI-HindIII fragment (IGF-I sequence) had been removed to give pMpGH(46)/human transcription factor Spl-lac Z fusion protein:

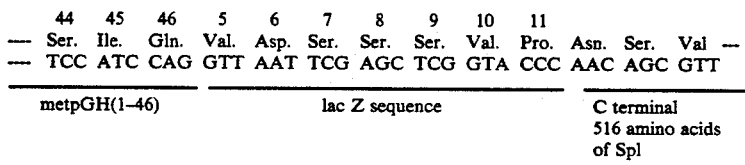

EXAMPLE 11

Production of construct proteins as inclusion bodies in E.coli

The pKT52 expression vector containing either
pMpGH(188)MIGF-I (Example 1),
pMpGH(191)N/IGF-I (Example 2),
pMpGH(88)CAFN/IGF-I (Example 3),
pMpGH(46)VN/IGF-I (Example 4),
pMpGH(11)VN/IGF-I (Example 5),
pMpGH(11)VN/R³IGF-I (Example 6),
pMpGH(42)FAHY/des(1-3)IGF-I (Example 7),
pMpGH(11)VNGFAHY/des(1-3)IGF-I (Example 8),
pMpGH(46)VNFAHY/chicken histone H2A.1 (Example 9) or pMpGH(46)/human transcription factor Spl-lac Z fusion protein (Example 10) was transformed into the lacI⁹ host, JM101 (j. Messing, Recomb. DNA Tech. Bull. Z, 42, 1979).

Cultures were grown in 13 liters of Min A broth at 37° C., 55% pO2 and pH 7.0 fed with glucose until the A600 was 15. Subsequently the cultures were induced with 1 g of IPTG for 5h. Inclusion body formation was monitored by phase contrast microscopy. Cells were harvested by centrifugation, suspended at 40% in 20 mM-Tris, 50 mM-NaCl pH 8.5 and homogenised at 9000 psi. The homogenate was diluted to 10% with water and the inclusion bodies collected by centrifugation. The inclusion bodies were washed by suspension in 20mM-Tris, 5mM-EDTA, 0.2% lysosyme, pH 8.0, incubated for 3h at 20° C., collected by centrifugation and the wet paste stored at −20° C.

Figure 2A:
Figure 2B:
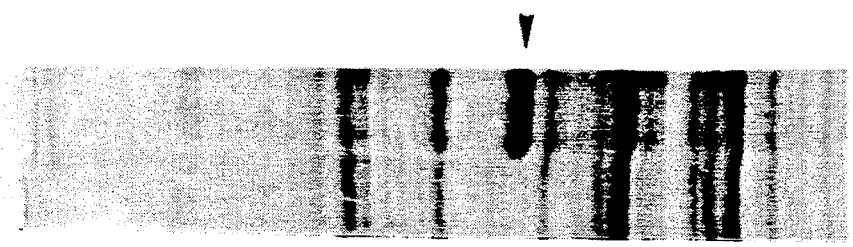

SDS polyacrylamide gel electrophoresis (SDSPAGE) of inclusion bodies from cultures transfected with the plasmids of Examples 4, 6, 7 and 8 are shown in FIG. 1, demonstrating the prominent bands of the respective fusion proteins. Lysates from cells grown in the absence=(U) and presence (I) of the inducer agent IPTG after SDSPAGE are illustrated in FIG. 2 for Examples 9 and 10. The induced bands are marked with arrows.

EXAMPLE 12

Figure 3:
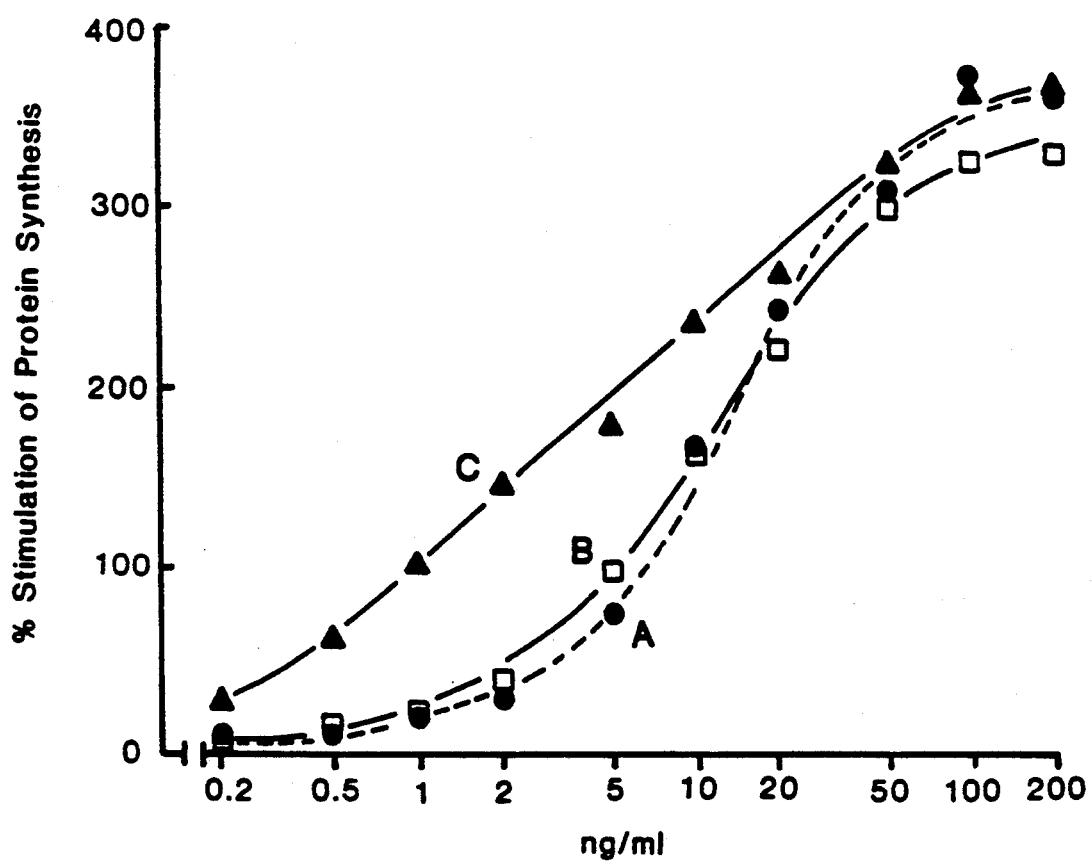
FIG. 3 shows dose-response curves of (A) IGF-I (Kabi), (B) IGF-I cleaved from MpGH(46)VN/IGF-I (Example 4) and (C) MpGH(ll)VN/R³IGF-I (Example 6).

Cleavage of fusion protein produced in inclusion bodies (Example 11) from E.coli transfected with pMpGH(46)VN/IGF-I (Example 4) and isolation of pure IGF-I The wet paste containing the construct proteins specified as in example 4 may be solubilised, the protein cleaved at the Asn/Gly bond, the resultant IGF-I folded and purified using methods familiar to those with knowledge of the prior art. These involved: dissolution of inclusion bodies in 8 M urea, 50n%M glycine, 10 mM EDTA and 1 mM DTE at pH 9.1; desalting into 8 M urea/50 mM glycine pH 9.2 on Sephadex G-25; cleavage for 4 h at 45° and pH 9.1 with the addition of 2.5 M NH2OH.HCl and 2.5 M LiOH; desalting as before; oxidation at a protein concentration of 1.25 mg/ml with 1.25 mM BME/0.1 mM oxidised BME at pH 8 and 25° in 2 M urea for 16h; C4 HPLC using 0.1% TFA and a propan-1-ol gradient; ion exchange chromatography on Mono S using an ammonium acetate gradient at pH 4.8; C18HPLC in 0.13% HFBA and elution with an acetonitrile gradient, followed by a final desalting into 0.1 M acetic acid. Cleavage and purification in this way of IGF-I derived from the pMpGH(46)VN/IGF-I construct yielded material that was equipotent with commercial recombinant IGF-I (Kabi) (see FIG. 3) in an assay that involves the stimulation of protein synthesis in rat L6 myoblasts (G. L. Francis et al. Biochem. J. 233, 207, 1986) as well as an IGF-I radioinunuunoassay (see FIG. 4).

EXAMPLE 13

Biological activity of the construct protein MDGH(11)VN/R³IGF-I

The product of Example 6 grown as an inclusion body according to Example 11 did not require cleavage in order to exceed the full biological activity of IGF-I.

Inclusion bodies were dissolved, desalted and oxidised as in Example 12. The refolding mixture was adjusted to 0.1% TFA, pH2.1 with HCl, filtered and pumped on to a $C_{18}$ column. Elution was effected with an acetonitrile gradient. The major protein peak was further purified by sequential HPLC steps involving an acetonitrile gradient in 0.13% HFBA on a $C_{18}$ column, an ammonium acetate gradient on a mono-S column and a propan-1-ol gradient in 0.13% HFBA on a $C_{18}$ column.

Figure 4:
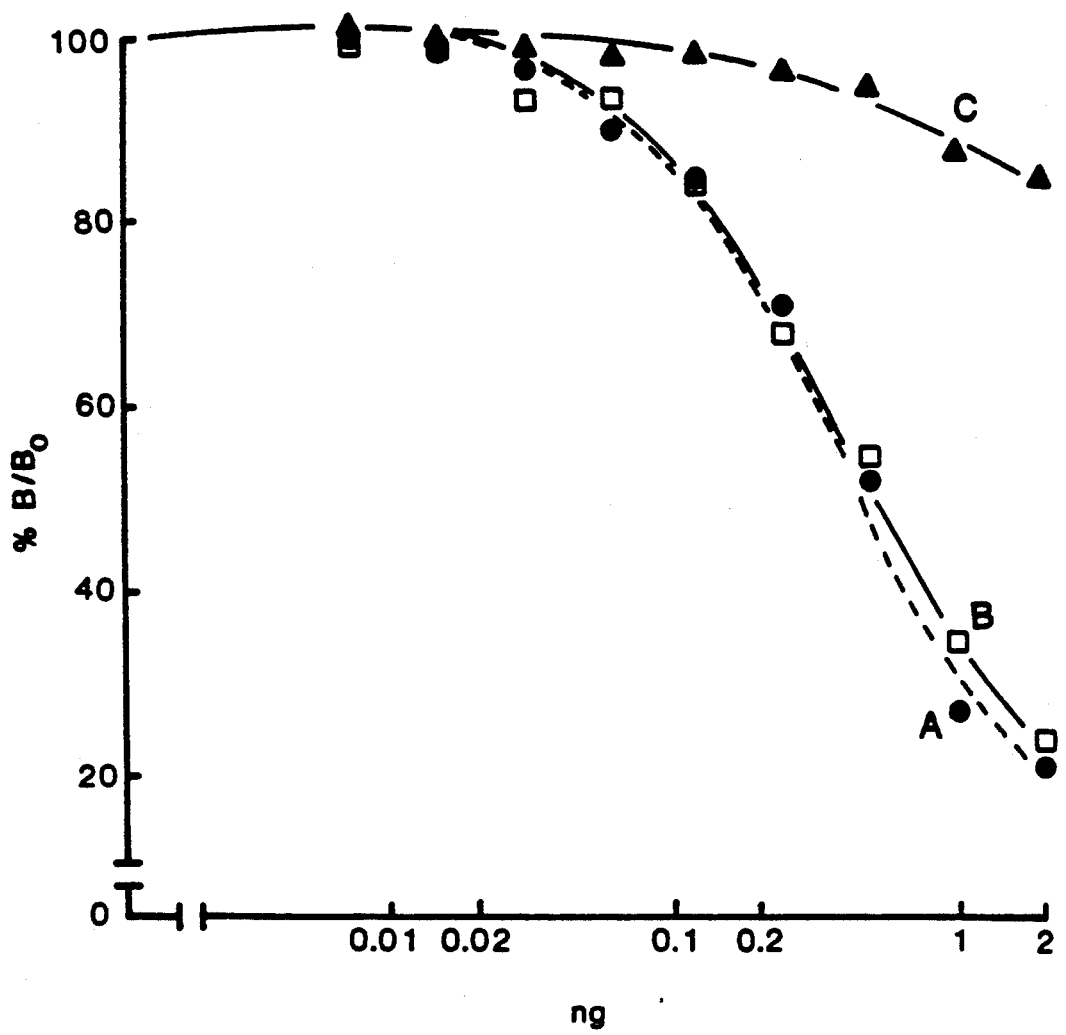
FIG. 4 shows IGF-I radioimmunoassay. IGF-I RIA of (A) IGF-I (Kabi), (B) IGF-I cleaved from MpGH(46)VN/IGF-I (Example 4) and (C) MpGH(ll)VN/R³IGF-I (Example 6).

The purification procedure yielded a single protein peak that accounted for approx. 30% of the protein in the refolding mixture. N-terminal sequence analysis confirmed the sequence as that expected for MpGH(11)VN/R³IGF-I. Biological assay as the percentage stimulation of protein synthesis above that in growth factor-free medium in rat L6 myoblasts (G. L. Francis et al. Biochem. J. 233, 207, 1986) gave a potency exceeding that of recombinant human IGF-I (Kabi) (see FIG. 3). The MpGH(11)VN/R³IGF-I cross-reacts only weakly in the IGF-I RIA (FIG. 4).

Finally, it is to be understood that various other modifications and/or alterations may be made without departing from the spirit of the present invention as outlined herein.

We claim:

1. A fusion protein exhibiting growth factor activity including:
   (a) a first amino acid sequence including the first 46 N-terminal amino acids of methionine porcine growth hormone (metpGH) selected from the group consisting of:
   MFPAMPLSSLFANAVLRAQHLHQLAADTYKEFERAYIPEGQRYSIQVN, and
   MFPAMPLSSLFANAVLRAQHLHQLAADTYKEFERAYIPEGQRYSIQVNFAHY; and
   (b) a second amino acid sequence for epidermal growth factor, joined to the C-terminal of the first amino acid sequence.

2. A fusion protein exhibiting insulin-like growth factor-I (IGF-I) or insulin-like growth factor-II (IGF-II) activity including:
   (a) a first amino acid sequence including the first 11 N-terminal amino acids of metpGH selected from the group consisting of:
   MFPAMPLSSLF-,
   MFPAMPLSSLFVN-,
   MFPAMPLSSLFVNFAHY- and
   MFPAMPLSSLFVNGFAHY-; and
   (b) a second amino acid sequence for IGF-I, IGF-II, or analogues thereof, joined to the C-terminal of the first amino acid sequence.

3. A pharmaceutical or veterinary composition for the treatment of growth hormone deficiencies or catabolic conditions in mammals or for increasing growth rates, redistributing nutrients or enhancing food conversion efficiency in mammals, said composition including an effective amount of:
   (a) a fusion protein exhibiting IGF-I or IGF-II activity including:
   (i) a first amino acid sequence including the first 11 N-terminal amino acids of metpGH selected from the group consisting of:
   MFPAMPLSSLF-,
   MFPAMPLSSLFVN-,
   MFPAMPLSSLFVNFAHY- and
   MFPAMPLSSLFVNGFAHY-; and
   (ii) a second amino acid sequence for IGF-I, IGF-II, or analogues thereof, joined to the C-terminal of the first amino acid sequence; and,
   (b) a pharmaceutically or veterinarily acceptable diluent, carrier or excipient therefor.

4. A method for the treatment of growth hormone deficiencies or catabolic conditions in mammals including those associated with infant prematurity, growth hormone deficiency, somatomedin deficiency, burns, infection, other trauma, cancer, cystic fibrosis, Duchenne muscular dystrophy, Becker dystrophy, autosomal recessive dystrophy, polymyositis as well as other myopathies, or for increasing growth rates, redistributing nutrients or enhancing food conversion efficiency in mammals, which method includes administering to a patient to be treated an effective amount of a fusion protein exhibiting IGF-I or IGF-II activity including:
   (a) a first amino acid sequence including the first 11 N-terminal amino acids of metpGH selected from the group consisting of:
   MFPAMPLSSLF-,
   MFPAMPLSSLFVN-,
   MFPAMPLSSLFVNFAHY- and
   MFPAMPLSSLFVNGFAHY-; and
   (b) a second amino acid sequence for IGF-I, IGF-II, or analogues thereof, joined to the C-terminal of said first amino acid sequence.

5. A method according to claim 4 wherein the fusion protein is administered at a dose rate of approximately 0.01 to 10 milligrams/kg body weight/day.

6. A method for improving the growth of cells in culture which method includes adding to a culture medium an effective amount of a fusion protein exhibiting IGF-I or IGF-II activity including:
   (a) a first amino acid sequence including the first 11 N-terminal amino acids of metpGH selected from the group consisting of:
   MFPAMPLSSLF-,
   MFPAMPLSSLFVN-,
   MFPAMPLSSLFVNFAHY- and
   MFPAMPLSSLFVNGFAHY-; and
   (b) a second amino acid sequence for IGF-I, IGF-II, or analogues thereof, joined to the C-terminal of said first amino acid sequence.

7. A plasmid encoding a fusion protein exhibiting IGF-I or IGF-II activity, said plasmid including as operatively joined components:
   (a) a suitable expression vector;
   (b) a first nucleic acid sequence encoding an amino acid sequence including the first 11 N-terminal amino acids of metpGH selected from the group consisting of:
   MFPAMPLSSLF-,
   MFPAMPLSSLFVN-,
   MFPAMPLSSLFVNFAHY- and
   MFPAMPLSSLFVNGFAHY-; and
   (c) a second nucleic acid sequence encoding a polypeptide for IGF-I, IGF-II, or analogues thereof, located 3' to said first nucleic acid sequence.

8. A process for the production of a fusion protein exhibiting IGF-I or IGF-II activity which process includes;
- (a) introducing into a unicellular organism a plasmid including as operatively joined components;
  a suitable expression vector containing
  a first nucleic acid sequence encoding an amino acid sequence including the first 11 N-terminal amino acids of metpGH selected from the group consisting of:
  MFPAMPLSSLF-,
  MFPAMPLSSLFVN-,
  MFPAMPLSSLFVNFAHY- and
  MFPAMPLSSLFVNGFAHY-; and
  a second nucleic acid sequence encoding a polypeptide for IGF-I, IGF-II, or analogues thereof, located 34' to said first nucleic acid sequence;
- (b) culturing the resultant organism;
- (c) expressing the polypeptide encoded by said DNA sequences; and
- (d) isolating said polypeptide from the culture.

9. A process according to claim 8 wherein the unicellular organism is an *E. coli* strain.

* * * * *